Figure 1A:

United States Patent [19]

Rabaud et al.

[11] Patent Number: 5,416,074
[45] Date of Patent: May 16, 1995

[54] ARTIFICIAL BIOLOGICAL MEMBRANE

[75] Inventors: Michel Rabaud, Talence; Francoise Lefebvre, S.-Medard-en-Jalles, both of France

[73] Assignee: Institut National de la Sante et de la Recherche Medicale, Paris, France

[21] Appl. No.: 842,185

[22] PCT Filed: Jul. 20, 1990

[86] PCT No.: PCT/FR90/00554

§ 371 Date: Mar. 20, 1992

§ 102(e) Date: Mar. 20, 1992

[87] PCT Pub. No.: WO91/01393

PCT Pub. Date: Feb. 7, 1991

[30] Foreign Application Priority Data

Jul. 20, 1989 [FR] France .................. 89 09798

[51] Int. Cl.$^6$ .................. C07K 15/20; A61K 37/12; A61K 9/00
[52] U.S. Cl. .................. 514/21; 530/353; 530/356
[58] Field of Search .................. 514/21; 530/353, 356

[56] References Cited

U.S. PATENT DOCUMENTS

| | | | |
|---|---|---|---|
| 4,347,234 | 8/1982 | Wahlig et al. | 514/801 |
| 4,600,533 | 7/1986 | Cher | 514/21 |
| 4,776,853 | 10/1988 | Klement et al. | 8/94 |
| 5,223,490 | 6/1993 | Rabaud et al. | 514/21 |

FOREIGN PATENT DOCUMENTS 0128706 12/1984 European Pat. Off.
WO86/05097 9/1986 WIPO

OTHER PUBLICATIONS

Kleinman et al., Analytical Biochemistry, 166, 1–13 (1987).
Murphy et al., Laboratory Investigation, 63, #3, 305–316 (1990).
Hansbrough et al., JAMA, 262, #15, Oct. 20, (1989).
Olivera et al., 22, 109–114, (1989).

Primary Examiner—Howard E. Schain
Assistant Examiner—P. L. Touzeau
Attorney, Agent, or Firm—Foley & Lardner

[57] ABSTRACT

The protein materials of the invention are essentially those obtained through reaction of a concentrated aqueous solution of type I and/or type III collagens and elastin or elastin peptides having a molecular weight above about 10,000, which can be dissolved in water. Preferred ratios of collagen reactants to elastin reactants in the process of the invention are in the range 1:10. The materials of the invention are obtained through solubilization of elastin.

29 Claims, 3 Drawing Sheets

ARTIFICIAL BIOLOGICAL MEMBRANE

BACKGROUND OF THE INVENTION

1. Field of the Invention

The invention relates to compositions of protein materials more particularly having properties of resiliency and robustness. It also relates to their preparation and their biological, biochemical and pharmacological applications, more particularly for the making of artificial biological membranes.

In its most widely accepted sense, the term "artificial biological membrane" covers membranes obtained from products of biological origin and used in very different fields, such as surgery, medicine, pharmacy, but also in the chemical, textile or paper-making industries.

The properties required for these applications are mainly properties of resilience, satisfactory mechanical behaviour, chemical resistance and compatibility with different media.

2. Related Art

As a constituent of such membranes it has already been suggested to use elastin, taking advantage of its properties of resilience and its both hydrophilic and hydrophobic nature.

For example, French Patent Application No. 85 03057 of 1 Mar. 1985 in the name of INSERM mentions a product based on elastin and soluble fibrin (i.e., fibrin monomers) which is particularly suitable for the making of biomaterials and support materials, such as artificial tissues or supports for cell cultures.

SUMMARY AND OBJECTS OF THE INVENTION

The search for materials more particularly adapted for carrying out grafts on narrow vessels led the Inventor of the Application to study the behaviour of different biological products in relation to a web of polymeric material acting as a support.

The work carried out has shown that reacting elastin or elastin derivatives in certain conditions with another protein of the connective tissue it is possible to obtain a protein material which adheres strongly to the support material used, has the properties of structural proteins and thus particularly satisfactorily meets the demands made on biological membranes.

It is therefore an object of the invention to provide novel compositions of protein materials which have important properties of resilience and robustness and if necessary of adhesion and retain their properties with various additives.

Another aim of the invention is to provide a process enabling said compositions to be readily obtained.

Yet another object of the invention is to supply biological membranes which can more particularly be used as artificial connective tissues and as support materials for cell cultures.

The compositions of protein materials according to the invention are essentially as obtained by the reaction of a concentrated aqueous solution of type I and/or III collagen and elastin or water-soluble elastin peptides having a molecular weight (MW) greater than approximately 10 000, as obtained by the solubilization of elastin.

In the following description the aforementioned elastin peptides will be referred to as "solubilized elastin peptides" and denoted by the abbreviation SEP.

Such a composition has properties of resilience and mechanical behaviour which enable it to be compared with structural proteins. It also has high adhesive properties which are particularly valuable for use in the biological applications envisaged.

A preferred composition of protein material is essentially as obtained by the reaction of elastin and type I and type III collagen. The proportion of type III collagen in relation to that of type I collagen is advantageously higher than 50% by weight, more particularly at least 70% by weight (dry weight). It will be noted that type III collagen as commercially available contains such quantities of type I collagen.

The elastin is an elastin of human or animal origin native or mature, or possibly their derivatives. It is generally elastin extracted from animal tissues, more particularly bovine nape ligament or porcine, bovine or human aorta.

Another preferred composition according to the invention is essentially as obtained by reacting solubilized elastin peptides and type III collagen.

According to one feature of the invention the collagen used in these compositions is collagen extracted from human placenta.

Unlike elastin, these compositions do not react with fibrin monomers.

According to a preferred feature of the invention the elastin or solubilized elastin peptides/collagen ratio (p/p, in relation to the dry weight) is approximately 10 to 1, preferably of the order of 2.5.

As a variant, the compositions according to the invention comprise a composite material in which the SEPs and the collagen are attached to a bone substitution material.

Advantageously the bone substitution material is selected from biocompatible materials having properties of osteoconduction (i.e., they are capable of being recolonized by organic or living structures capable of producing bone, due to their surface properties and their porosity) and of osteinduction (i.e., they are capable of creating an environment favourable to the triggering of osteogenesis).

Such materials are more particularly based on $Ca^{++}$, tricalcic phosphate or apatites. One particularly suitable material is hydroxy-apatite.

The invention therefore relates to compositions as obtained by reacting hydroxy-apatite with SEPs and type I and/or III collagen.

The process for the preparation of the compositions of protein materials defined hereinbefore is characterized in that it comprises:

the bringing into contact with a concentrated aqueous solution of type I and/or III collagen, in conditions allowing the formation of a gel, of elastin or elastin peptides having a MW at least equal to approximately 10 000, said peptides being soluble in a 50—50 mixture of tertiobutylic alcohol-1M potassium hydroxide in water, the recovery of the gel formed and its subsequent treatment, if desired.

The collagen concentration of the aqueous solution is approximately at least 3 mg/ml, more particularly of the order of 3 to 10 mg/ml.

In one preferred embodiment of the invention, the contacting stage is performed in physiological conditions—i.e., at approximately 37° C. with a pH of the order of 7 to 7.5.

The elastin or the SEPs are respectively in suspension or dissolved in a buffer of pH 7 to 7.5, preferably pH 7.4, whose constituent elements encourage or at the very least do not impede the required reaction. Buffers containing, for example, $Na^+$, $Ca^{++}$ and/or $Mg^{++}$ cations, $PO_4^=$ and/or $Cl^-$ anions appear advantageous in this respect.

A particularly appropriate buffer which contains all the aforementioned ions is formed by the PB buffer, which has the following molar composition: 1 mM $PO_4$, 150 mM NaCl, 2 mM $Ca^{++}$, 1 mM $Mg^{++}$.

Gels which are particularly resistant to crushing by the finger are obtained from buffer elastin or SEP and collagen used in a ratio of approximately 2.5.

This ratio can be modified in accordance with the application of the composition.

The elastin is generally obtained from animal tissues by dissolution and elimination of the accompanying proteins.

The tissues preferably used are bovine nape (neck) ligament or porcine or bovine aorta.

The elastin peptides originate, for example, from the hydrolysis of elastin by alkaline treatment, more particularly with 1M potassium hydroxide, acid treatment, for example, with oxalic acid, or enzyme treatment with elastase.

The collagen originates more particularly from human placenta.

To obtain membranes which can be used in the application envisaged hereinafter, there are successively added to the SEPs additives which enable the qualities of the gel to be improved and confer thereon properties useful in the application envisaged, then collagen.

Amongst the advantageous additives used on their own or in combination, fibronectin and laminin may be quoted, which encourage the cohesive qualities of the gel; type IV collagen, which improves adhesive qualities; growth hormones, nutrient elements, vitamins, proteoglycanes, such as heparin and dermatane sulphate, enzymes, antiseptics, catalysts or oxido reducers. These additives preserve the structure of the protein materials according to the invention.

Numerous other additives, therapeutic and antibacterial agents can be used and will readily be selected by the skilled addressee in relation to the required properties and used in the appropriate metered quantities, having regard to the applications envisaged.

The mixture formed is then incubated at a temperature of the order of 37° C. until the gel forms. The various elements of the mixture can be satisfactorily dispersed by using a, for example, VORTEX ® type mixer.

If the composition is to be given a required shape and size, the reaction is performed in an appropriate mould, making use of the modulable nature of the compositions according to the invention. In this way the composition to be used can be obtained as a biomaterial in the form of tubes, filaments or strips.

The composition is demoulded and if necessary dried to eliminate the water surplus.

Preservation is performed in the wet condition in the presence of an antiseptic or in the lyophylized state. In that case the product is rehydrated by bringing it into contact with sterile physiological water prior to utilization.

To obtain compositions formed by composite materials, advantageously the bone substitution material is reacted with SEPs and then with collagen. The temperature and pH conditions are more particularly as indicated hereinbefore.

As already stated, the compositions according to the invention have remarkable properties of resilience and robustness and also high hermeticity, biocompatible and if necessary adhesive properties.

These properties are more particularly advantageous for the production of artificial biological membranes.

The invention is therefore also aimed at membranes characterized in that they comprise a composition of protein materials as defined hereinbefore.

These membranes have a very special advantage when used as artificial connective tissues.

In constitution they are very close to the lamina densa of the basal membranes and more particularly, when they contain type III collagen, of the arterial subendothelium.

The membranes according to the invention can be used more particularly as closure, support and reinforcing members.

They can form temporary supporting members enabling the process of tissue repair to be initiated, then guided.

They are applied by means of biocompatible glues or fixed by sutures. As a variant, their high adhesive properties enable them to be attached to the required place without the use of other means.

According to one very advantageous feature of the invention, the membranes adhere strongly to the polymeric supporting materials normally used as webs in the preparation of biomaterials.

It may also be noted that they encourage scarring.

It will be noted that the membranes advantageously cause no coagulation, since they are free of fibrin and do not become fixed to fibrin.

They enable certain tissue losses to be compensated in the treatment of burns.

They are also very advantageous for making narrow artificial vessels.

In a general way the membranes according to the invention can be used in all fields of surgery, more particularly digestive, vascular, urinary, genital and obstetric, maxillo-facial and plastic, dermatological, foetal and neonatal, and also in veterinary surgery.

The selection of one or more particular additives enables appropriate membranes to be readily obtained for a given application.

Thus, considering, for example, proteoglycanes as additives, membranes can be prepared which can be used as arterial subendothelium by using heparane sulphate, or else cartilage-substitute membranes with sulphate chondroitins. Similarly, to reconstitute an epidermis-dermis interface, it is more particularly advantageous to add keratane sulphate to the compositions according to the invention.

The invention therefore provides a skilled addressee with the means of producing a membrane adapted to his or her requirements.

The membranes according to the invention also form particularly useful supporting materials for cell cultures.

Varied cell cultures can be developed, operating in normal conditions, by the use of the supports. We may quote more particularly cultures of smooth muscle cells, fibroblasts, keratinocytes, epithelial cells and endothelial cells. The yields obtained are high.

These membranes also act as a skin base when epithelial cells are seeded with a view to reconstituting a piece of epidermis. The latter can then be transplanted to the organism of a receiver.

The membranes produced from the composite materials stated hereinbefore, more particularly those containing hydroxy-apatite with SEPs and callogen can be used as supports for osteoblast cultures.

The membranes based on composite materials take the form of gels. The centrifugation residues can be used in biochemical studies.

The invention also relates to kits containing the elements required to put into effect a tissue repair or a cell culture.

The following merely illustrative Examples indicate other features and advantages of the invention.

Figure 1B:
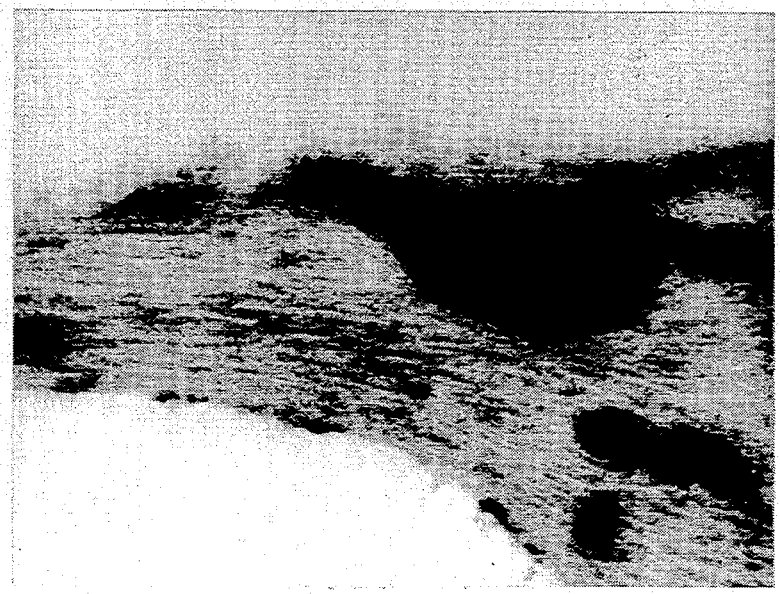
Figure 2:
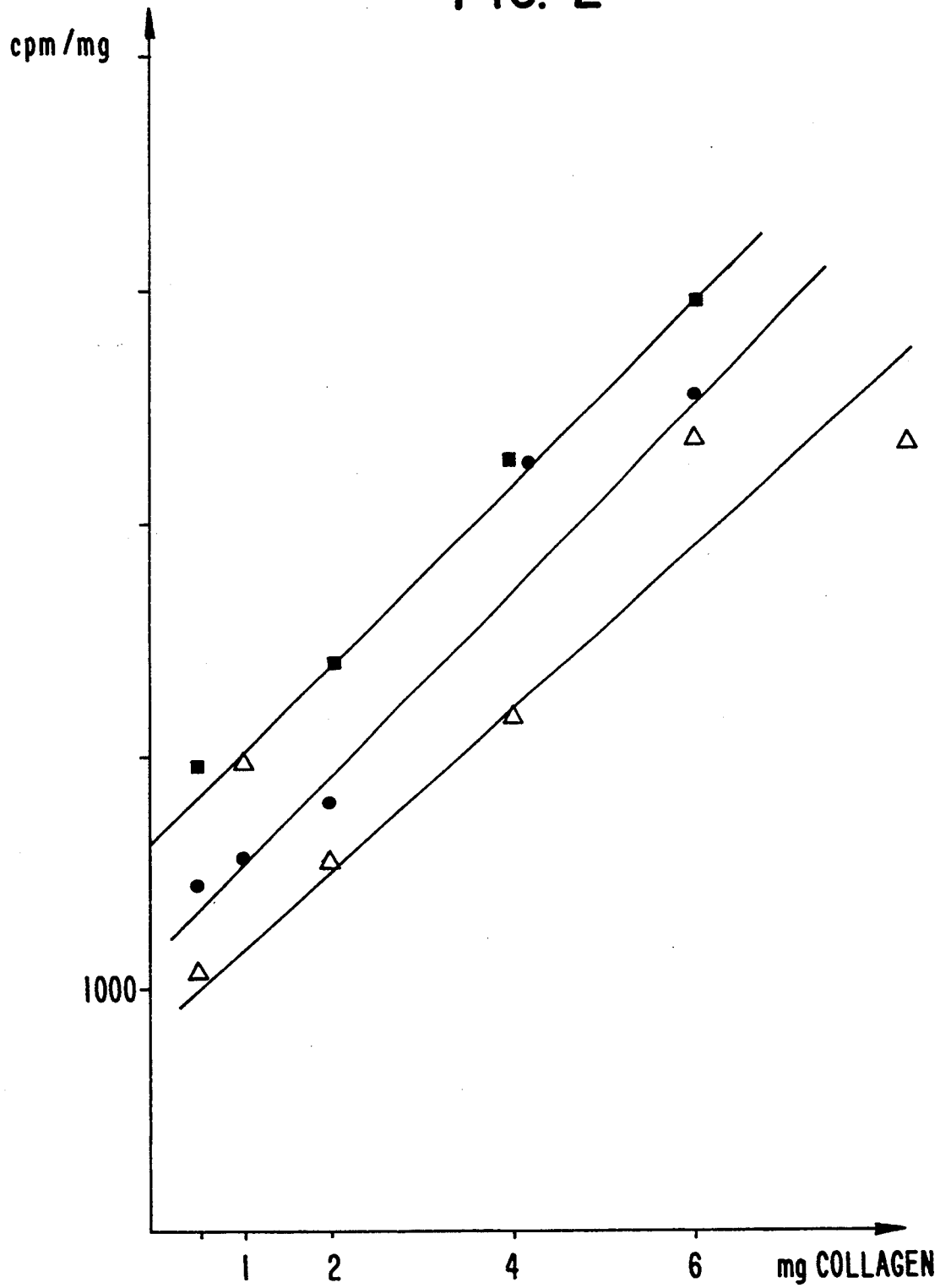
Figure 3:
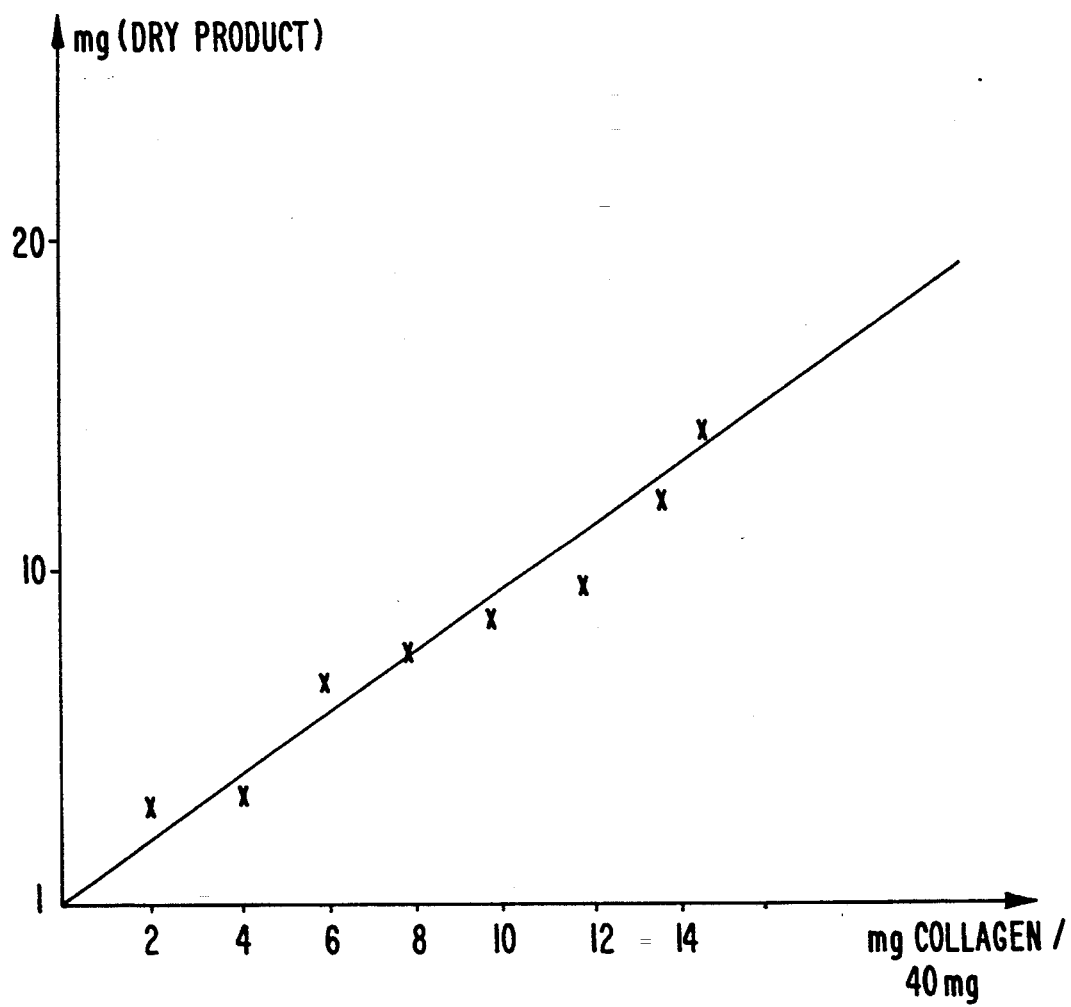

In the figures referred to in the Examples:

FIGS. 1a and 1b are different enlargements of sweeping electron microscope photographs of protein materials according to the invention, FIG. 2 shows a variation in quantity in mg of dry product as a function of the quantity of collagen added in mg (test with 40 mg of SEP), and FIG. 3 shows the radioactivity, in cpm/mg of the washed centrifugation residue, corresponding to a composition according to the invention, as a function of the quantity of collagen added and the reaction time.

The elastin used in these Examples is commercially available SIGMA elastin originating from bovine nape ligament.

Type I+III collagen or type III collagen and fibronectin are products marketed by the Mérieux Institute and are obtained from human placenta. The type I+III collagen contains 73% type III and 27% type I.

EXAMPLE 1: PREPARATION OF ELASTIN-COLLAGEN GEL 1 ml of type I+III collagen gel were added either at a rate of 3 mg/ml or 6 mg/ml to a suspension of 40 mg crushed and screened elastin in 1 ml of PB buffer of pH 7.4 (1 mM $PO_4$, 150 mM NaCl, 2 mM $Ca^{++}$, 1 mM $Mg^{++}$). Homogenization was performed by VORTEX® for 5 seconds, whereafter the mixture was poured into a mould at 37° C. without agitation for 15 minutes, 1, 2, 12 hours. The product was recovered, washed and dried.

As a variant, instead of pouring the mixture into a mould, incubation was performed in a receptacle, whereafter the product formed was separated by centrifugation (10 min/3000 rpm). The recovered product took the form of a single homogenous phase.

The structures were studied using a sweeping electron microscope. This technique allowed the observation by immediate analysis of a very close association between the elastin and the collagen (cf. FIG. 1a (enlargement×5600) and FIG. 1b (enlargement×33600)).

EXAMPLE 2: PREPARATION OF SOLUBILIZED ELASTIN PEPTIDES-COLLAGEN GEL

*PREPARATION OF THE SOLUBILIZED ELASTIN PEPTIDES 1 g of elastin was used. After crushing and screening, the elastin was put into suspension of 50 ml of tertiobutylic alcohol. 50 ml of 1M potassium hydroxide were added to the water with adequate agitation to maintain an emulsion. At 25° C. the elastin was completely dissolved after 48 hours.

Then 50 ml of water was added and neutralization was performed to pH 7 by the addition of acetic acid.

The tertiobutylic alcohol, the salts and the peptides having a molecular weight lower than or equal to approximately 10000 were eliminated by dialysis for about 14 hours against running water.

Then dialysis was performed against permuted water (2 baths of approximately two hours).

The preparation was frozen at −40° C. and lyophylized for purposes of preservation. The yield was 65 to 85%.

STUDY OF THE STABILITY OF THE GEL OBTAINED 50 mg of peptides obtained from the solubilization of the elastin and tagged with iodine$^{125}$ were solubilized in 2 ml of PB. 2 ml of collagen III solution in water ( 10 mg/ml ) were added. Homogenization was performed by the VORTEX® (5 seconds). The whole was placed on a water bath at 37° C. for 5 hours. Centrifugation was performed for 10 minutes at 6000 rpm. The residue was washed with 5 ml of water for 15 minutes, then with 5 ml of water for 1 hour, and then with 5 ml of water until the following day. After each washing the radioactivity of the residue was measured.

The product was then left for 7 days and another series of washings with water was carried out. The washed product was placed in water at 25° C. for 18 days without changing its appearance. After centrifugation the product was dried in air (25°–29° C.) for two days.

The result was a highly resistant compact material, although during the washings it had been fairly disintegrated for reasons of efficient operation. At that time when taken up in water it provided a more plastic matrix which was not solubilized in the presence of ½ acetic acid(pH≈1) but in the long run gave a gel which was fairly similar to the first one.

* REACTION OF THE SEPs WITH COLLAGEN

1st experiment: using SEPs not tagged with iodine$^{125}$ increasing metered quantities of SEPs—of 0 5, 10, 20, 30, 40, 60 and 100 mg in 1 ml PB 7.4 at 37° C. —were brought into contact with 1 ml of the collagen I +III gel (3 mg/ml) and then homogenized (5 seconds, VORTEX®).

It was observed that the gels formed more quickly and took a more compact form in proportion to the quantity of SEPs.

Centrifugation for 10 minutes at 5000 rpm enabled the gels to be separated after 1 hour: from 5 to 20 mg SEPs they were soft; from 30 to 100 mg SEPs they were much firmer. The gels most resistant to crushing under the fingers were those obtained with 30 and 40 mg of SEPs. The gels were dried in air and weighed. A certain proportionality was observed in the weight obtained in relation to the weight of SEPs.

2nd experiment: operations were performed as indicated hereinbefore, using metered quantities of 10, 20, 30, 40, 60 and 80 mg of SEPs in 1 ml of PB, pH 7.4 and 1 ml of I+III collagen.

With 40 mg of SEPs, 1, 2 and 3 ml of collagen solution were used.

3rd experiment: operations were performed as indicated hereinbefore, but with a fixed quantity of SEPs (40 mg/ml) and increasing metered quantities of I+III collagen (10 mg/ml)—i.e., 2, 4, 6, 8, 10, 12, 14 and 20 mg.

The gel rapidly coagulated from 6 mg onwards, the tubes at 14 and 20 mg being much more opaque. For their decantation H₂O/EtOH was added prior to centrifugation. All the gels obtained were washed and dried on filter paper. Fairly good proportionality was observed between the quantity of product obtained after the drying of the gel and the quantity of collagen (cf. FIG. 2).

4th experiment: to study SEP-collagen gels, use was made of SEPs tagged with iodine$^{125}$ and a determination was made of the events produced by the measurement of the radioactivity retained on the precipitate.

A solution of SEP-I$^{125}$ was prepared with 5 mg/ml and 4600 cpm/mg, to which the increasing metered quantities of collagen: 0.5, 1, 2, 4 and 6 mg were added, preceded with the adequate quantity of PB buffer (7.4) for a final volume of 2 ml. The gel formed satisfactorily.

Centrifugation was performed for 30 to 40 minutes at 5 500 rpm, whereafter the radioactivity of the supernatant, the crude residue and then the residue washed twice with H₂O was measured.

The experiment was carried out over variable times: 1, 2 and 4 hours.

Results obtained are presented in FIG. 3, which gives the measurement of the radioactivity (cpm/mg) on the washed residue as a function of the quantity of collagen by weight in relation to the time of the experiment.

The curve with the symbols corresponds to an experiment lasting for 1 hour, that with the symbols O to a duration of 2 hours and that with the symbols Δ to a duration of 4 hours.

EXAMPLE 3: PREPARATION OF GELS COMPRISING FIBRONECTIN, LAMININ AND TYPE IV COLLAGEN

Tagged fibronectin was used in solution in a PO₄ buffer (0.1M, NaCl 0.15 pH 7.2) with 1.2 mg/ml and 8.10$^6$ cpm/mg.

SEPs were prepared with 10 mg/ml PB (7.4). To 1 ml of this solution 10, 20, 50, 100 and 200 μl of the solution of fibronectin-I$^{125}$ were added. Incubation was performed for 30 minutes at 37° C. and 0.4 ml of I+III collagen and the qsp (appropriate quantity) of PB (7.4) was added for a final volume of 2 ml. Homogenization was performed with the VORTEX® (5 seconds) and the whole was kept without agitation for 4 hours at 37° C. Centrifugation at 5500 rpm for 40 minutes enabled the residues and supernatants to be separated.

It was observed that the addition of fibronectin accelerated gel formation: it was formed instantaneously with 200 μl of fibronectin. Repeated washings, at first brief and in water, and then for approximately 14 hours in water at 20° C. on an average reduced the radioactivity retained in the gel and carried by the fibronectin by only 17%, something which demonstrates the importance of the affinity of fibronectin in relation to the constituents of the gel.

Use was made of tagged laminin (Sigma) and type IV collagen (Mérieux) in solution in the 0.1M PO₄ buffer used in the test with fibronectin—laminin 500 000 cpm/ml, IV collagen 850,000 cpm/mg.

SEPs were prepared with 10 mg/ml in PB (7.4). To 1 ml of this solution 10, 20, 50, 100 and 200 μl of the laminin or IV collagen solution was added. Incubation was performed for 15 minutes at 37° C. Qsp of PB (7.4) and 0.4 ml of I+III collagen were added for a final volume of 2 ml. Homogenization was performed with the VORTEX® (5 seconds) and the whole was kept without agitation for 4 hours at 37° C. Centrifugation at 5000 rpm for 40 minutes enabled the residues and supernatants to be separated.

It was found that the resulting gel was more compact in proportion as the quantity of laminin or IV collagen was higher. Repeated or prolonged washings did not release the radioactivity connected with the residues, something which demonstrated an important affinity with these 2 proteins.

EXAMPLE 6: STUDY OF THE PROPERTIES OF ADHESION OF SEP-COLLAGEN GEL TO DACRON®

A prosthesis sample of Dacron® (a cylinder 1 cm in length and 0.6 cm in diameter) was placed for incubation in PB buffer (pH 7.4) for 4 hours. During the same time the SEP-collagen gel was prepared by operating as follows: 0.6 ml of TPS (pH 7.4) and 0.4 ml of type III collagen (10 mg/ml) were added, taking good care to homogenize between each addition. The whole was left for 4 hours at 37° C. Then centrifugation was performed for 10 minutes at 5000 rpm and the residue was washed twice with 2 ml of permuted water (pH 6). For the length of prosthesis used, twice this quantity of gel was adopted.

Then the gel was applied by spatula inside the Dacron® material while drawing it out, whereafter it was allowed to dry in air for approximately 14 hours. A prosthesis was obtained which was slightly less flexible but which had retained radioactive material.

The prosthesis was then washed with water (2 ml) without too violent agitation for 5 hours, the water being renewed after each measurement. At the 6th hour the prosthesis was plunged in a beaker containing 100 ml of water with fairly vigorous magnetic agitation. During all these washings the radioactivity remaining on the prosthesis was evaluated up to the 23rd hour.

The results obtained showed that the SEP-collagen gel appeared to be fairly well retained on the Dacron®, although it had not been strongly fixed. This experiment also confirmed that as well as being adhesive, the material was insoluble in water.

EXAMPLE 7: PREPARATION OF A COMPOSITE MATERIAL BASED ON HYDROXY APATITE, SOLUBILIZED ELASTIN PEPTIDES AND COLLAGEN

First of all hydroxy-apatite (referred to hereinafter as hA) was reacted with SEP-1$^{125}$ at 37° C. (pH 7.4). An hA-SEP-I$^{125}$ product was obtained which had fixed 25 to 30% of the radioactivity.

Then this product was reacted with type I+III collagen at 37° C. and pH 7.4.

The resulting product was a composite material of hA-SEP-collagen type which took the form of a gel around hA which remained firmly fixed after a number of washings.

Advantageously SEP was used at the rate of 20 mg/ml. The association sites offered by hA were saturated with 2×1 ml after 15 minutes of incubation at 37° C.

The reaction of hA-SEP with collagen was performed, for example, with 40 mg of hA-SEP, 1.2 ml of buffer (pH 7.4) and 0.8 ml (8 mg) of I+III collagen.

We claim:

1. A proteinaceous composition that is a product of a process comprising the step of contacting reactants (A) and (B), under physiological conditions of approximately 37° C. and a pH in the range of from 7.0 to 7.5, wherein (A) comprises a concentrated aqueous solution of at least one material selected from the group consisting of type I and type III collagen, wherein (B) comprises elastin or water-soluble elastin peptides having a molecular weight greater than approximately 10 000, said peptides obtained by the solubilization of elastin, and wherein the ratio of reactant (A) to reactant (B) is in the range of from 1.0:10.0 to 1.0:1.5 by dry weight.

2. Compositions according to claim 1, wherein the ratio of reactant (A) to reactant (B) is in the range of from 1.0:2.0 to 1.0:5.0.

3. Compositions according to claim 1, wherein the ratio of reactant (A) to reactant (B) is approximately 1.0:2.5.

4. Compositions according to claim 1, wherein both type I and type III collagens are reacted with (B).

5. Compositions according to claim 4, characterized in that the proportion of type III collagen is greater than 50% of the total weight of reactant (A) by dry weight.

6. Compositions according to claim 4, characterized in that the proportion of type III collagen is greater than 70% of the total weight of reactant (A) by dry weight.

7. Compositions according to claim 1, wherein the collagens reacted with (B) consist of type III collagens.

8. Compositions according to claim 1, further comprising a bone substitute material wherein said material possesses the properties of osteoconduction and osteoinduction.

9. Compositions according to claim 8, in which said bone substitute material comprises calcium.

10. Compositions according to claim 9, in which said bone substitute material is one or more chosen from the group consisting of calcium phosphates, calcium apatites and hydroxyapatites.

11. Compositions according to claim 10, in which said bone substitute material is a hydroxyapatite.

12. A process for the preparation of proteinaceous compositions comprising the steps of:

(1) contacting reactant (A) with reactant (B), under physiological conditions of approximately 37° C. and a pH in the range of from 7.0 to 7.5, said conditions allowing for the formation of a gel, and (2) recovering the gel formed thereby, wherein reactant (A) comprises a concentrated aqueous solution of at least one material selected from the group consisting of type I and type III collagen, wherein reactant (B) comprises elastin or water-soluble elastin peptides having a molecular weight greater than approximately 10 000, said peptides being soluble in a 50/50 mixture of tertiobutylic alcohol-1M potassium hydroxide in water; and wherein the ratio of reactant (A) to reactant (B) is in the range of from 1.0:10.0 to 1.0:1.5 by dry weight.

13. The process of claim 12, further comprising the step of:

(3) treating the gel formed thereby to form artificial connective tissues or support materials for cell cultures.

14. A process according to claim 12, wherein step (1) is performed in a buffer of pH 7.0 to 7.5, and said buffer contains one or more of $Na^+$, $Ca^{++}$ or $Mg^{++}$ as a cation, and one or more of $PO_4^=$ or $Cl^-$ as an anion.

15. A process according to claim 14, wherein said buffer comprises approximately 1 mM $PO^4$, 150 mM NaCl, 2 mM $Ca^{++}$, and 1 m$Mg^{++}$.

16. A process according to claim 12, wherein one or more compounds selected from the group consisting of fibronectin, laminin, collagen IV, therapeutic agents and antibacterial agents are added to said solubilized elastin peptides of reactant (B).

17. The process of claim 12, wherein said concentrated aqueous solution further comprises said bone substitution materials.

18. Artificial biological membranes comprising proteinaceous compositions according to claim 1.

19. An artificial connective tissue comprising a composition according to claim 1.

20. Physical supports for cell cultures comprising compositions according to claim 1.

21. Membranes according to claim 18, which are shaped into the form of tubes, filaments, cylinders or strips.

22. Physical supports for cell cultures according to claim 20, formed or molded into shapes useful for the culture of smooth muscle cells, fibroblasts, keratinocytes, epithelial cells or endothelial cells.

23. Compositions according to claim 9, which are formed of molded into physical supports for cell cultures.

24. Materials according to claim 23, useful for osteoblast cultures.

25. Compositions according to claim 9, wherein said material is biocompatible.

26. A composition according to claim 1, comprising one or more additives selected from the group consisting of fibronectin, laminin, collagen IV, growth hormones, nutrient elements, vitamins, proteoglycans, enzymes, antiseptics, catalysts and oxido-reducers.

27. A composition according to claim 18, comprising one or more additives selected from the group consisting of heparin sulphate, chondroitin sulphate and keratan sulphate.

28. Composition according to claim 18, wherein said compositions adhere to polymeric supporting materials.

29. Compositions according to claim 28 wherein said supporting materials are used as webs in the preparation of biomaterials.

* * * * *